United States Patent
Ludington et al.

(10) Patent No.: US 6,402,369 B1
(45) Date of Patent: Jun. 11, 2002

(54) ARRAYABLE THERMAL ASSAYS

(75) Inventors: David Norman Ludington, Newton, PA (US); Thomas Louis Fare, Redmond, WA (US); Dominic Joseph Lo Iacono, Yardville; Timothy James Davis, Columbus, both of NJ (US); Helen Jiang Semus, Bensalem; Paul John Stabile, Langhorne, both of PA (US); Frank Guarnieri, Brooklyn, NY (US); Russell Todd Granzow, Titusville, NJ (US); Peter J. Zanzucchi, Lawrenceville, NJ (US); William Chiang, Monmouth Jct., NJ (US)

(73) Assignee: Sarnoff Corporation, Princeton, NJ (US)

( * ) Notice: Subject to any disclaimer, the term of this patent is extended or adjusted under 35 U.S.C. 154(b) by 0 days.

(21) Appl. No.: 09/432,736

(22) Filed: Nov. 2, 1999

Related U.S. Application Data

(60) Provisional application No. 60/112,629, filed on Dec. 16, 1998, and provisional application No. 60/106,811, filed on Nov. 3, 1998.

(51) Int. Cl.[7] .............................................. G01N 25/00
(52) U.S. Cl. .............................. 374/13; 374/11; 374/33; 374/179; 422/51; 136/204; 136/224; 436/147; 435/288.4
(58) Field of Search .............................. 374/13, 11, 12, 374/10, 31, 33, 34, 179; 422/51; 136/204, 224, 201; 436/147; 435/288.4, 287.1

(56) References Cited

U.S. PATENT DOCUMENTS

| | | | |
|---|---|---|---|
| 3,059,471 A | 10/1962 | Calvet | 374/10 |
| 3,319,456 A | 5/1967 | Speros et al. | 374/11 |
| 3,643,491 A | 2/1972 | Dell et al. | 374/11 |
| 4,255,961 A | 3/1981 | Biltonen et al. | 374/11 |
| 5,288,147 A | 2/1994 | Schaefer et al. | 374/10 |
| 5,439,291 A | 8/1995 | Reading | 374/11 |
| 5,525,300 A | * 6/1996 | Danssaert et al. | 435/288.4 |
| 5,707,149 A | * 1/1998 | Freire et al. | 374/33 |
| 5,819,842 A | * 10/1998 | Potter et al. | 165/206 |
| 6,079,873 A | * 6/2000 | Cavicchi et al. | 374/10 |
| 6,106,784 A | * 8/2000 | Lund et al. | 422/104 |

FOREIGN PATENT DOCUMENTS

| WO | 80/00878 | 5/1980 | .................. 374/13 |
|---|---|---|---|

* cited by examiner

*Primary Examiner*—Diego Gutierrez
*Assistant Examiner*—Stanley J. Pruchnic, Jr.
(74) *Attorney, Agent, or Firm*—William J. Burke

(57) ABSTRACT

Provided are, among other things, devices for and methods for performing thermal signature assays on a two or more samples in an array, using active/control base thermopiles, the method comprising: [a] performing a heat transfer to the two or more samples in each of a two or more containers, using at least one base thermopile in thermal communication with the two or more containers; and [b] determining a total heat transferred to the samples by the base thermopile in step [a]; and [c] sensing in real time a temperature difference between a first sample and a second sample of the two or more samples resulting from performing step [a].

16 Claims, 4 Drawing Sheets

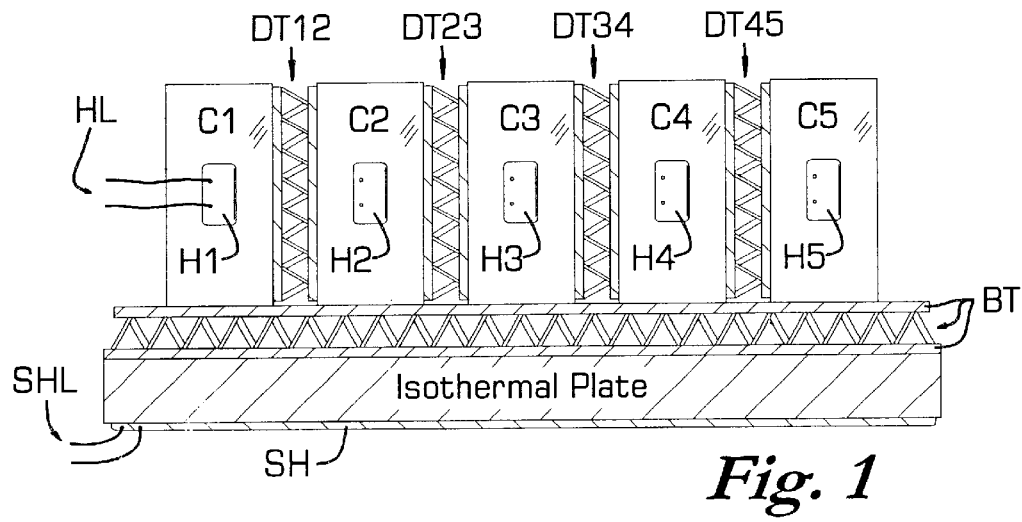
*Fig. 1*
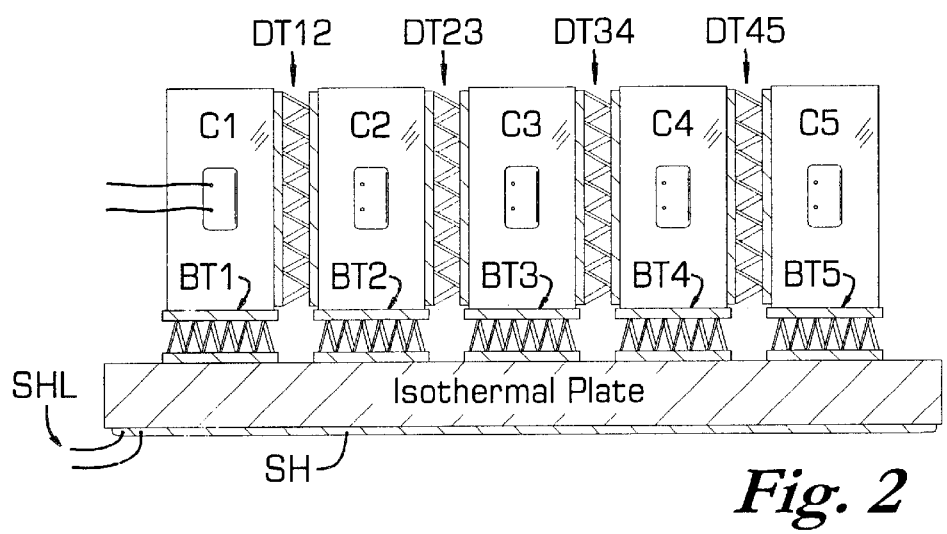
*Fig. 2*
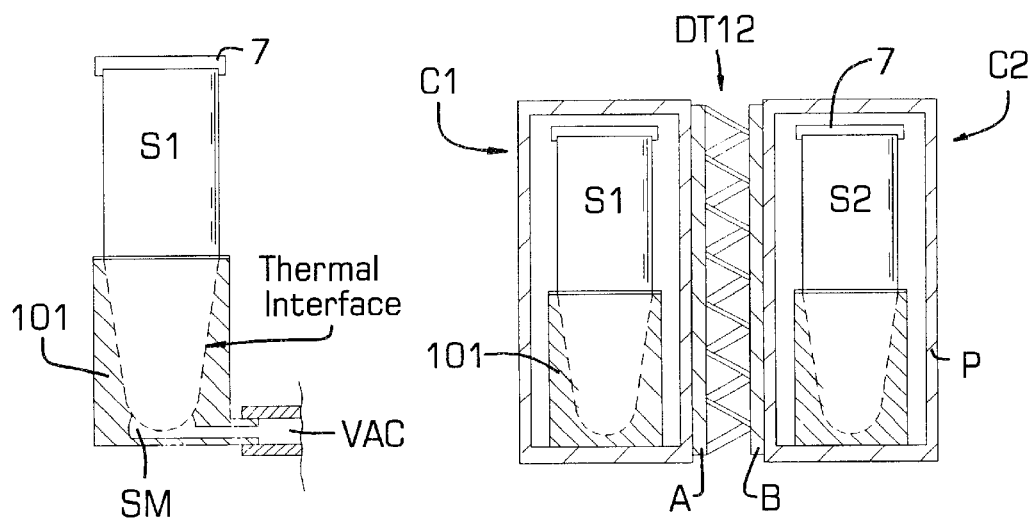
*Fig. 3*   *Fig. 4*

ARRAYABLE THERMAL ASSAYS

This application claims the priority of Stabile et al., "Nanothermal Array Screening Pharmaceutical, Genomics and Diagnostics," U.S. Provisional Application No. 60/112, 629, filed Dec. 16, 1998 and Ludington et al., "Arrayable Approaches To Thermal Measurements" U.S. Provisional Application No. 60/106,811, filed Nov. 3, 1998.

This invention relates to arrayable thermal or calorimetric measurement systems allowing precise, reproducible calorimetric assays for physical characterization of biochemical products, as well as for use in pharmaceutical and biotechnology product development. Specifically, this invention uses a novel calorimetric method and apparatus employing base thermopiles in thermal communication with a plurality of samples, to provide thermal signatures, such as changes in specific heat capacity or capacitance, to differentiate or rank biological or chemical samples. This allows systems having arrays of cells, and using facile automated handling, such as by use of disposable tubes, microtiter plates, robotic transports, and the like to perform thermophysical assays, such as for sample screening or to characterize chemical or biological activity.

Biological calorimetry is a well known technique used as a marker to identify systems, or to detect phase transformations or reactions such as binding of ligands to proteins (see A. E. Beezer, *Biological Calorimetry*, © 1980, Academic Press, New York). Useful measurements for calorimetric assays include the derivative with respect to temperature of a unique state function, the enthalpy H, yielding the heat capacity $$C_p = d\, H(T)_p / dT \tag{1}$$

at constant pressure p. Direct calorimetric measurements allow determination of the heat capacity $C_p$ of a sample, measured in kJ/K or similar units. By determining heat capacity in a selected temperature region, one can determine the enthalpy H, and in turn other state functions such as the sample entropy S, and the Gibbs Function G. See P. W. Atkins, *Physical Chemistry*, $6^{th}$ Ed., W. H. Freeman and Company, New York © 1997, ISBN 0716728710. It is useful to note that heat capacity is an intensive property, independent of the quantity or shape of the substance under consideration. The corresponding extensive property is known as heat capacitance, in analogy with electrical capacitance, and is a function of the quantity of substance involved.

Many processes involving biopolymers and proteins take place with detectable changes in apparent heat capacities of the reacting species. A molecule or biochemical system that has or obtains many translational, rotational, and vibrational degrees of freedom will have a high heat capacity Cp while a simpler (e.g., folded protein) system will have a lower heat capacity. Determining the heat capacity $C_p$ therefore yields an important thermophysical property, and can be used for assays and structure determinations for solutions, proteins, and biological samples. Such assays and structure determinations can be useful for sample screening and biochemical product synthesis.

Six possible sources of large heat capacity (and entropy) changes have been identified for processes involving proteins (Julian M. Sturtevant, *Proc. Natl. Acad. Sci. USA*, Vol 74, No. 6, pp.2236–2240, June 1977). Protein structure changes such as unfolding can produce large changes in heat capacity, such as unfolding of α-Chymotrypsin, which yields a change in heat capacity $C_p$ of +3080 cal/K/mol at neutral pH. Processes include hydrophobic effects, where nonpolar groups raise the heat capacities of solutes in aqueous solutions; electrostatic effects, where creation of positive and negative charges in aqueous solutions leads to a negative change in heat capacity; breaking of hydrogen bonds with increasing temperature, where heat capacity increases; intramolecular vibrations, affected by chemical changes such as unfolding or ligand binding, where an increase in the number of easily excitable internal vibrational modes results in heat capacity increases; or changes in equilibria, where an actual shift with temperature of an equilibrium between two or more states will appear experimentally as a contribution to the heat capacity.

Current views about protein-ligand interactions state that electrostatic forces drive the binding of charged species and that burial of hydrophobic and polar surfaces influences or controls the heat capacity changes associated with the reaction. However, concerning interactions of a protein with a monovalent cation where electrostatic forces are expected to be significant due to the ionic nature of the ligand, heat capacity changes are expected to be small due to the small surface area involved in the protein-ligand recognition event. It has been found, however, that with the physiologically important interaction of Na+ with thrombin, binding is characterized by a modest dependence on ionic strength, but a large negative heat capacity change of –1.1 ±0.1 kcal/mol/K (see Guinto, Cera, *Biochemistry*, Vol 35, No 27, pp. 880–8804). It is proposed that this change is linked to electrostatic effects can reveal a binding or folding event where water molecules are buried, resulting in significant heat capacity changes independent of changes in exposed hydrophobic surface or coupled conformational transitions (rotations about a single chemical bond). Generally, monovalent cation binding to proteins is a widespread phenomenon and can play an important role in enhancing catalytic activity of enzymes. Potassium ion binding to proteins is typically accomplished mainly through two mechanisms. In one mechanism, K+ forms a ternary complex with the enzyme and substrate (e.g., ATPases). In another mechanism, as seen in pyruvate kinase, K+ binds to a distinct site and influences the activity of the enzyme in an allosteric fashion, thereby causing a change in the function of the enzyme. Sodium binding can also be important, for example, Na+ activated enzymes are involved in blood coagulation and complement cascades.

Solvation of charged and polar groups is typically accompanied by a negative heat capacity change which is small and only known for simple molecules. Heat capacity of water molecules sequestered in the interior of a protein is significantly lower than in bulk water, because of reduced mobility and more ordered structure. Burial of water molecules linked to ligand binding or protein folding can result in large negative heat capacity changes, which can be detected in an assay using the disclosed invention.

As another example, the binding of L-aribinose and D-galactose to the L-aribinose-binding protein of Escherichia coli has been studied by isothermal and scanning calorimetry (see Fukada, Sturtevant, *Journal of Biological Chemistry*, Vol. 258, No. 21 pp. 13193–13198, 1983). It is found that the binding reaction with arabinose is characterized by an enthalpy change of –15.3 kcal/mol, with a large decrease in apparent heat capacity of –0.44 kcal/mol/K. However, determination methods used are painstaking, typically done with two samples at a time (such as an experimental sample and a control or reference sample), and involve elaborate experimental and chemical procedures.

Thermophysical assays have the advantage of not requiring the use of any external or added agents, such as fluorescent or radioactive tags, which can cause damaging or unknown perturbations on a biochemical system. The heat capacity $C_p$ is also an equilibrium property that can be used to great advantage. Thus, while a small molecule ligand that does not bind to a protein should have a negligible effect on the heat capacity of a system, a small molecule that does bind usually causes a permanent change in molecular degrees of freedom, and hence the heat capacity $C_p$ of the system. Many measurements can thus be made at leisure, after the binding event.

Thermophysical assays can also elucidate cellular processes. One especially important cellular protein, calmodulin (CAM), appears to be at the junction of many signal transduction processes. CAM appears to be able to modulate many distinct processes because it can exist in a large ensemble of different structural states, presenting a corresponding large ensemble of chemical interaction sites. As with most molecular structures, each distinct state is likely to have a characteristic heat capacity $C_p$ Elucidating the network of signal pathways through CAM via heat capacity characterizations would likely have enormous implications for the pharmaceutical industry. Another area where thermophysical techniques can give information about cellular mechanisms is the possibility of elucidating the action of rapamycin, which has been observed to cause immunosuppression by interfering with a calcineurin pathway. Calcineurin is a CAM-dependent phosphotase.

Presently, direct calorimetric observations are made using painstaking physical methods of thermal analysis to determine enthalpy changes in a sample under study. In one known method, isothermal titration calorimetry, a first solution containing a ligand is incrementally titrated (using a gear-driven plunger that actuates a syringe) into a second solution containing a macromolecule or other receptor. Heat released or absorbed upon interaction of the two solutions is measured and plotted as a function of time. As the macromolecule becomes saturated with ligand, the binding heat signal decreases until full saturation, where only background heat from dilution of the ligand is detected. See *Nature*, Vol. 384, pp. 491–492, Dec. 5, 1996; also Freire, E., Mayorga, O. L., Straume, M., *Analytical Chemistry*, Vol. 62, pp. 950A–959A (1990). A serious drawback to this technique is the high relative quantities of reactant-containing solution required, and the titration or metering hardware needed makes arrayable assays difficult, particularly if the samples are later to become part of a further synthesis or the making of a dosage form.

Two other typical known techniques used are Differential Scanning Calorimetry (DSC) and Differential Thermal Analysis ( DTA). In DTA, a single heater imparts thermal energy to both a sample pan and a reference or control pan at a constant predetermined rate, such as can be measured in calories/hour, joules/sec, or similar units. When a thermodynamic change occurs in the sample (e.g., a binding event), or if there is an inherent difference in heat capacitances between the sample and reference, there is a resultant temperature difference $\Delta T$, which is proportional to the enthalpy change $\Delta H$, the heat capacity $C_p$, and the total thermal resistance R. This thermal resistance is common to both DTA and DSC, and has two components, $R_0$ and $R_S$:

$$R=R_0+R_S \qquad (2)$$

$R_0$ is the inherent thermal resistance of the instrument, due to the thermal separation of the sample, heater and thermometer or temperature measuring device(s). $R_S$ is the thermal resistance of the sample itself, and includes other peripheral factors like the imperfect thermal contact between the sample and its container or pan. Because thermal resistance $R_S$ is a property of the sample, in DTA, $R_S$ cannot be determined through a calibration with the reference. As a result, a plot of $\Delta T$ is dependent on the sample, making calculation of heat capacitance and heat capacity $C_p$ very difficult.

Differential scanning calorimetry (DSC) is a well-known method used worldwide to study energetic changes in solid or liquid samples with high precision and accuracy. DSC has been used to determine affinity of a set of azobenzene ligands for streptavidin (see Weber, P. et al., *Journal of the American Chemical Society*, Vol. 16, pp. 2717–2724, 1994). In DSC, a power compensation technique is used via two separate heaters, and two control loops that operate to keep the sample and reference at the same temperature. A first control loop regulates the average heating rate of both the sample and reference, and a second control loop provides a differential thermal power input q to eliminate any temperature difference between the sample and reference due to an inherent thermophysical difference in the sample or due to a thermodynamic change, such as a heat of reaction. Associated with the second control loop, the rate of this differential thermal power input q to the two heaters, dq/dt, (the derivative of q with respect to time t) is recorded and can be related to the heat flux by $$dH/dt=-dq/dt+(C_S-C_R)dT/dt-RC_{Sd}^2q/dt^2 \qquad (3)$$

With a constant ambient pressure to which the sample and reference are subjected, dH/dt is simply the rate of absorption of heat per unit time; dq/dt is equal to the differential power input; $C_S$ and $C_R$ are the heat capacities of the sample and reference, respectively; T is temperature in Kelvin; and R is the thermal resistance given above. The second term on the right is negligible provided the sample and reference have comparable heat capacities; the last term on the right results from thermal lag and can be minimized by making the sample and reference as small as possible, reducing $R_S$. This reduces thermal resistance R from above equation (2) to an acceptable level. Under these conditions, integration of the data curve will yield, to a good approximation, $$C_p=d\ H(T)_p/dT \sim -dq/dt \qquad (4)$$

DSC techniques and numerical methods are known in the art. See J. L. Naughton, C. T. Mortimer, *Thermochemistry and Thermodynamics*, ed. H. A. Skinner, Butterworths, London, Vol. 10, © 1975. For larger sample sizes, the above thermal lag can be corrected by use of the Tian equation and conversion to an alternate excess heat capacity versus temperature scan (see Frederick P. Schwartz, *Biochemistry*, Vol. 27, pp. 8429–8436).

Both the DTA and DSC techniques have serious limitations. One limitation involves the high accuracy required for DSC and DTA measurements. For macromolecular interactions, for example, when active concentrations fall below 0.3 percent, the effects on the heat capacity $C_p$ become negligible, making only a contribution of heat capacity of 1/10 percent ($10^{-3}$) of the total. Determining differences in heat capacity $C_p$ in solutions containing macromolecules in such a solution requires an exceptionally accurate calorimetric measurement. Newer scanning microcalorimetry techniques are often used to determine relative heat capacity $C_p$ within 0.002 percent. However, these thermal techniques are limited by the small sample quantities available and the relatively high amount of experimental effort required for accurate measurements. Homogeneous preparations of high quality biological specimens cannot always be obtained.

As a result, heat capacity for systems of biological interest is generally measured using "van't Hoff analysis" and not direct calorimetric determinations, which cannot be carried out in a system where the ligand binds in the millimolar range (*Biochemistry*, Vol. 35, No. 27, pp. 8800–8804, 1996). This type of analysis arises from solving the Gibbs-Helmholtz equation, and plotting 1n K versus 1/T, where K is the relevant reaction rate or equilibrium constant for the reaction under study, and assuming that the heat capacity changes are constant over a temperature range of interest, e.g., 5° C. to 45° C. The analysis involves determining the reaction rate K in non-calorimetric ways that make arrayable assays difficult.

There is therefore a need for a system and method allowing micromethods that facilitate arrayable thermal assays. Such a system should be able to provide information about the relative binding affinities of different ligands for a receptor protein, for many samples simultaneously. A calorimetric assay system is also needed to facilitate screening of combinatorial libraries, which are collections of chemical or biochemical compounds synthesized by combining chemical "building blocks" or groups as reagents, typically in a combinatorial or quasi-combinatorial manner. An enormous number of compounds can be created, with theoretically distinct compounds numbering in the millions or billions ($10^9$). Combinatorial libraries can be screened, for example, by examining the extent of binding of a reagent with a target molecule of interest. A filamentous phage display peptide library (which is a form of combinatorial library created by recombinant technology) can be screened for binding to a biotinylated antibody, or other receptor. Often, library screening techniques require the use of chemical labels or tags. There is a real need for acquiring relative binding affinities for a large number of samples in a short time without the use of chemical markers. For isothermal titration calorimetry, Differential Scanning Calorimetry (DSC) and Differential Thermal Analysis (DTA), the approach is time consuming. Three thermal scans per day are routine, and relatively large sample sizes limit productivity.

Generally, as sample size gets smaller, the surface/volume ratios increase, allowing a lower thermal resistance $R_S$, and the smaller mass facilitates timely ramping of temperature with minimum error. It is desirable to have a calorimetric system allowing arrayable measurements, and yet minimal and constant heat exchange properties which do not vary from assay to assay. A high assay throughput is desired, consistent with desired accuracy, and the need for consistent, reproducible results for each assay. A desirable system should be able to detect denaturation, ligand binding, and other changes with active molecules in the millimolar range or less.

However, thermophysical assay apparatuses meeting these requirements are quite difficult and subject to noise and error. A high degree of temperature measurement sensitivity is required, with minimum detection thresholds of 10 microKelvin or less, and even less allowable temperature error.

A number of problems make arrayable thermophysical assays difficult. With any temperature driven assay system, thermal leakage due to conduction, convection and thermal ($T^4$) radiation can skew results, sometimes unpredictably. Thermal leakage includes both leakage or coupling in the ambient space around samples to be tested, and also cross-talk, where thermal energy intended for one sample is coupled to another, or where one sample "warms" another.

Thermal gradients are also problematic, because it is difficult to maintain across an array temperature uniformity to the thresholds required, particularly when a system is temperature driven using resistive tapes or other discrete heat sources. Close packing of samples in an array can minimize the effect of thermal gradients, but one then risks introducing another large source of error, because closely packed samples increase the effect of cross-talk. Tight temperature regulation whereby samples are temperature-driven to be the same temperature during the course of testing can reduce the effect of cross-talk, as discussed below.

The adequacy of thermal contact between samples and their respective containers, and test cells or heat input/temperature sensing devices also introduces a source of error, although usually one can in large part compensate for differences in thermal resistance R and conductance by prior calibration and the use of reference samples or cells, containing substances of known composition and thermal characteristics (e.g., lab grade pure deionized water).

With use of electrical sensing/control devices for temperature sensing down to under 10 micro Kelvin sensitivity, and the use of active devices for heat input, electrical noise and drift can cause problems, particularly when amplifiers are presented with absolute DC signals that tend to cause drift and other errors.

It is one object of this invention to permit arrayable thermal assays using thermoelectric devices, where reliable relationships between electric potential differences and temperature differences are exploited in solid or liquid materials, with switching made possible between active (heat input) and control (sensing) modes. It is another object to provide arrayable assay techniques that measure either heat capacity, and/or heat gained or lost in real time, inside samples where active macromolecules or other reactants are only in the millimolar range or less. It is yet further an object of the invention to allow simplified feedback control of an arrayable thermal assay, and to have need for fewer reference samples of known composition to reduce errors, using dual data feeds from thermoelectric devices. It is yet a further object to make thermal assays arrayable by compensating for, and avoiding, thermal (temperature) gradients across an array, using thermoelectric devices. It is yet a further object to reduce electrical noise and measurement error in the temperature sensing functions of such a thermophysical assay. Other objects will become apparent upon reading of the specification.

SUMMARY OF THE INVENTION

Using the teachings of this invention, one can measure heat capacities and generate thermal signatures as a function of temperature and time for thermal assay arrays, and compensate for or avoid problems associated with thermal temperature gradients across the array that can make accurate measurements difficult. One can also use disposable sample containers and make measurements quickly while driving the assay at the same time. The invention includes a method for performing thermal assays (e.g., thermal signature assays) on a two or more samples in an array, using active/control base thermopiles, the method comprising one or more of the following:

(a) performing a heat transfer to the two or more samples in each of a two or more containers, using a base thermopile in thermal communication with the two or more containers, or using a local heater in thermal communication with the two or more containers;

(b) determining a total heat transferred to the samples by the base thermopile in step (a);

(c) sensing in real time a temperature difference between a first sample and a second sample of the two or more samples of step (a), wherein, in one embodiment, the sensing in real time is performed by a differential thermopile or an individual base thermopile;

(d) performing an additional heat transfer adjustment on the basis of the temperature difference, the additional heat transfer adjustment sized and targeted to at least one of the first and second samples to drive the temperature difference toward zero between the first and second samples;

(e) determining the size of the additional heat transfer adjustment during step (d) for each of the first and second samples;

(f) comparing the size of the additional heat transfer adjustment during step (e) for each of the first and second samples, and ranking the first and second samples according to their respective additional heat transfer adjustments during step (e);

(g) determining heat capacitance for each of the first and second samples using any of: the total heat transferred in step (b), and the additional heat transfer adjustment during step (d);

(h) calculating from the heat capacitances determined in step (g), the heat capacity ($C_p$) for each of the first and second samples; and (i) comparing the size of the additional heat transfer adjustment during step (e) for each of the first and second samples, and generating therefrom a thermal profile (e.g., signature) from successive applications of the method during a ramp in temperature of at least one of the first and second samples.

The base thermopile can be electrically driven via the Peltier effect, and the heat transfer using the base thermopile can occur with respect to an isothermal plate in thermal communication with a junction of the base thermopile. The isothermal plate can also be in thermal communication with a strip heater, and the method can additionally comprise ramping the temperature of the isothermal plate using the strip heater.

Optionally, step (a) can comprise transferring heat to the sample using an individual base thermopile in thermal communication with fewer than all of the samples in the two or more samples in the array.

The invention includes this method wherein the heat transfer adjustment comprises applying heat directly using a local heater. Such a local heater can be selected from the group consisting of a resistive device; a non-ohmic device; a device utilizing electromagnetic induction as an energy transfer method; a device operating primarily by light emission; a sonic device; a speaker; a device using combustion-based heating; a device that mediates exposure to one or more heat sinks, using at least one barrier; a chemical device utilizing a phase transformation of a substance for heating; a mechanical system to convert mechanical energy to heat energy; and a device using Bernoulli flow of a carrier medium to transfer heat.

Step (d) can additionally comprise calculating total net heat transferred (or a thermal denaturation curve) to characterize denaturation of a protein or nucleic acid; a binding event; a chemical reaction; a phase transformation, or a change in the basal or metabolic state of a cell, cellular components, or tissue. The total heat transferred in step (b) can be determined by monitoring the control voltage of the base thermopile. Step (a) can also comprise applying an AC waveform to drive the base thermopile, thereby creating a time varying rate of heat transfer by the base thermopile.

Step (a) can comprise applying an AC waveform to drive the local heater, thereby creating a time varying rate of heat transfer by the local heater. Also, the heat transfer using the local heater can occur with respect to an isothermal plate in thermal communication with the local heater. An isothermal plate can be in thermal communication with a strip heater, and the method additionally can comprise ramping the temperature of the isothermal plate using the strip heater.

The invention can also include teachings relating to an arrayable thermal assay apparatus using active/control base thermopiles for performing thermal assays on a two or more samples in an array, the apparatus comprising one or more of the following:

(1) a base thermopile (BT) in thermal contact with a two or more containers, in the array, each of the two or more containers retaining one of the two or more samples;

(2) a differential thermopile with a first opposed thermal junction in thermal contact with a first container, and a second opposed thermal junction in thermal contact with a second container;

(3) first and second local heaters in individual thermal contact with the first and second containers, respectively, wherein the base thermopile is configured and driven to perform a heat transfer to the two or more containers, and the differential thermopile is configured and monitored to sense a relative temperature difference between the first and the second containers; and wherein the first and second local heaters are configured and driven to perform an additional heat transfer adjustment on the basis of the relative temperature difference. The two or more containers can comprise wells in a microtiter plate. Also, the base thermopile can be an individual base thermopile in thermal communication with fewer than all of the samples in the two or more samples in the array. The individual base thermopile can be configured and monitored to sense a relative temperature difference between the first and the second containers.

Optionally, the first and second local heaters are individually selected from a heater group consisting of a resistive device; a non-ohmic device; a device utilizing electromagnetic induction as an energy transfer method; a device operating primarily by light emission; a sonic device; a speaker; a device using combustion-based heating; a device that mediates exposure to one or more heat sinks, using at least one barrier; a chemical device utilizing a phase transformation of a substance for heating; a mechanical system to convert mechanical energy to heat energy; a device using Bernoulli flow of a carrier medium to transfer heat.

Optionally, one can also add a correlated double sampling system to reduce noise and drift from calorimetric determinations, the correlated double sampling system comprising:

an input amplifier connected to provide gain for a thermopile output signal from at least one thermopile selected from the group consisting of a base thermopile and a differential thermopile;

an AC coupled amplifier connected to provide gain to an input amplifier output signal from the input amplifier;

a sample and hold circuit having a sample and hold input connected to an output signal of the AC coupled amplifier;

a chopper circuit to cycle an input amplifier input signal to the input amplifier between the thermopile output signal and a reference voltage, and to also cycle synchronously the sample and hold input between an AC coupled amplifier output signal from the AC coupled amplifier and the reference voltage.

BRIEF DESCRIPTION OF THE DRAWINGS

FIG. 1 shows a cross sectional schematic view of a thermal sensing array according to the invention, using differential thermopiles and a single base thermopile;

FIG. 2 shows a cross sectional schematic view of a thermal sensing array according to the invention, using differential thermopiles and individual base thermopiles;

FIG. 3 shows a combination cross sectional/surface view of a sample and sample holder used in the thermal sensing array of FIGS. 1 and 2;

FIG. 4 shows a combination cross sectional/surface view of a pair of samples and sample holders inside respective cells, separated by a differential thermopile, such as used in the thermal sensing array of FIGS. 1 and 2;

DEFINITIONS

Figure 5:
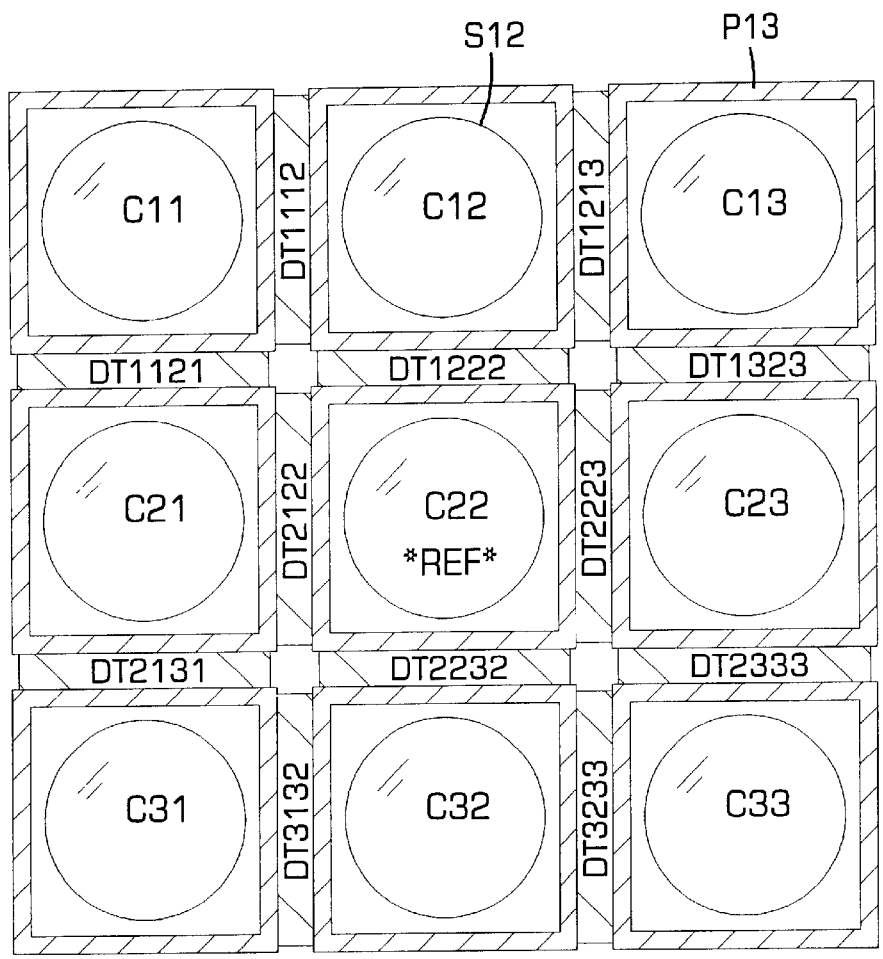
FIG. 5 shows a possible cross sectional top view of cells and differential thermopiles of a 3×3 cell thermal sensing array using either base thermopiles or individual base thermopiles.

The following definitions shall be employed throughout:

"AC" (alternating current) shall denote any electric current that reverses direction, perhaps periodically; or any applied potential of changing polarity. AC waveforms shall refer to any part or component of such alternating currents, such as a rectified square waveform comprising repeated single polarity pulses (see pulses below), with or without additional DC components.

"Acoustic" can refer to sound waves in air, but more generally can include any alteration of properties of whatever elastic medium is used in or about the samples to be assayed. Possible elastic media include dry nitrogen or other gases; water; oil; propylene glycol; refrigerants, such any of the compounds bearing the trademark, Freon® (aliphatic organic compounds containing the elements carbon and fluorine, and other halogens such as chlorine and hydrogen); sand; and the like. Properties that can be altered include pressure, particle or molecule displacement, or density. Most commonly, this is achieved using longitudinal compressive waves in the elastic medium, provided by a speaker (see definition below), but it can also occur by using jets or flow of the elastic medium.

"Active" in the context of a thermopile shall denote an active heat transfer mode using the Peltier or other effects or devices with similar physical characteristics.

"Additional Heat Transfer Adjustment" shall include any or all individual additional heat transfers to one or more samples in an array, whether by use of a base or individual thermopile, or a local heater.

"Array" shall include any mechanical or electromechanical means for accommodating two or more containers that allow practicing this invention, such as by use of a carrier, which encompasses a platform or other object that can support such a plurality of containers. This shall include multiwell microplates, microtiterplates, and any combination of carriers. Such carriers can be translatable or rotatable via a servo-driven device.

"Base Thermopile" shall denote a thermopile in thermal communication with at least one sample, but not with any two of its opposed thermal junctions between or immediately adjacent to two different samples. A common thermopile in thermal communication with all samples in an array meets this definition so long as it does not comprise opposed junctions between any two samples (see differential thermopile).

"Bias" shall refer to any average direct current (DC) voltage applied to a conductor. This shall include alternating current (AC), AC waveforms, or pulses that when averaged over time reveal a non-zero DC applied overall voltage.

"Container" shall comprise any vessel or chamber into which a sample can be placed, such as reaction tubes, microtiter plates, microfuge tubes, pipettes, or micropipettes (e.g., with capacities of 0.5 milliliters or less), including the lambda, straight bore, or Levy types.

"CPU" (Central Processing Unit) shall denote any decision processing device that performs the functions given; this definition shall encompass all processors, but does not preclude analog electrical circuits that perform the same functions.

"DC" (direct current) shall denote any quasi-static electric current that flows in one direction only, or any applied potential of single unchanging polarity.

"Differential thermopile" shall denote a thermopile with its two opposed thermal junctions, or at least two opposed thermal junctions in thermal communication with (between or immediately adjacent to) two separate samples. A single thermopile placed in thermal communication between two sample cells or containers in an array meets this definition so long as it operates primarily to sense temperature or transfer heat between two samples, not between a sample and an isothermal plate, or between a sample and an ambient surface such as a heat sink or finned radiator (see base thermopile).

"Driver" shall include all devices that give power or control signals to operate one or more devices, such as base thermopiles or heaters; this shall include drivers that also act to monitor the action of the operated devices by measuring or integrating supply currents, control signals, and the like.

"Drive . . . Toward Zero" shall mean to effect a physical change to urge a quantity such as differential temperature toward zero, either asymptotically, or using any other method, including methods having "overshoot," so long as a running average of the quantity (e.g., temperature) tends to zero.

"Heat of Reaction" shall include thermal energy released or absorbed from exothermic and endothermic reactions, respectively.

"Individual Base Thermopile" shall denote a thermopile in thermal communication with an individual sample, or a subset of samples (less than all samples) in an array.

"Isothermal Plate" can be synonymous with the isothermal plane, but not necessarily planar in shape. Generally, isothermal plate shall denote any body used as a heat sink or thermal buffer to interface with at least one junction of one or more thermopiles.

"Pulse" shall refer to quick variation of applied potentials which are otherwise constant, or nearly constant. This variation shall be of finite duration in relation to the charge decay or charge leakage on a substrate. In shape, a pulse or series of pulses can resemble spikes or parts or components of AC waveforms.

"Ramping" shall include actions that cause positive upward movement of temperature, or negative (downward) movement of temperature.

"Ranking" shall include ordering of a two or more samples according to some detected aspect of their respective thermal signatures, such as heat capacity $C_p$ or detected heat of reaction or increase in enthalpy H.

"Receptor" shall include any molecule or target molecule, or portion thereof, that can combine with a ligand, and can include peptides; proteins; single-stranded, double-stranded, or triple-stranded nucleic acids; enzymes; non-enzymes; monomeric and multimeric proteins; oligonucleotides; synthetic oligonucleotides; portions of recombinant DNA molecules; or portions of chromosomal DNA. The molecular structure associated with such a receptor can include substitution with substituents including cofactors, coenzymes, prosthetic groups, lipids, oligosaccharides, phosphate groups, benzene or aromatic groups, fluorescent tags, fluorophores, and the like.

"Sensing in Real Time" shall denote sensing or measurement intended to reveal the resultant heat of reaction or a processing step, e.g., resistive or thermoelectric heating, as a function of time.

"Speaker" can refer to any loudspeaker, transducer, machine, or device, such as a piezoelectric device, that is capable of providing acoustic energy, such as through pressure modulation; more generally, it is any device capable of altering the properties of the medium used in and about the samples to be assayed.

"Strip Heater" shall include any heating device in thermal contact with an isothermal plate.

"Thermal Contact" shall include all thermal energy exchanged between two entities, and shall comprise thermal (contact) conduction; convection currents in any fluid medium; and thermal (black body) radiation.

"Thermal Denaturation Curve" shall include any plot or data set characterizing a physical change (e.g., heat capacity $C_P$), such as a physical change associated with: [1] denaturation of a protein or nucleic acid; [2] a binding event or reaction inside a sample; [3] any phase transformation (e.g., crystallization) in a sample. Such a data set can be a function of temperature, or any other parametric form, such as a plot as a function of time.

"Thermal Signature" shall refer to any detectable thermal change or event, such as a change in heat capacity or capacitance; the result of a phase transformation or crystallization; denaturation, such as due to folding or unfolding, coiling or uncoiling, or twisting or untwisting, either full or partial, in any combination, of a molecule in a sample. Such a thermal change or event can result from or encompass a release of photons, such as fluorescence; changes in molecular structure, such as denaturation; absorption of light, such as ultraviolet light; changes in electromagnetic polarization properties, either for light or fluctuating electric fields of low frequency; changes in enzyme activity or electron affinities, introduction of ionic species in solution; and the like "Thermopile" shall include any thermoelectric device utilizing the Seebeck or Peltier effects, or any other thermoelectric effect, to [1] effect a heat transfer between two opposed physical junctions ("hot," "cold") or [2] to sense or produce a signal indicative of a temperature difference between two opposed physical junctions. Emphasis in this disclosure is on conventional thermopiles, which comprises a number of connected thermocouples; however, a single thermocouple shall meet this definition.

This definition shall also include any and all thermoelectric devices that use the Thomson effect, where temperature gradients in a single material subject to electric current flow will absorb or emit heat. It also includes thermopiles in conjunction with magnetic fields, such as devices employing the Nernst, Ettingshausen and Righi-Leduc effects, where an applied potential difference, the magnetic field direction, and the direction of the temperature gradient or heat flow are mutually perpendicular.

This definition also shall allow for any devices that are or can be made to be functionally equivalent to a thermopile, including a plurality of nominally distinct devices in any combination, operating together or adjacent to one another, that can comprise or utilize: any heat producing device, including resistive heaters, inductive heaters, or combustion based heating; exposure to one or more heat sinks, mediated by modulating one or more barriers; laser or other light emission/absorption systems; chemical devices, including those utilizing a phase transformation of a substance for heating; mechanical systems that convert motion to thermal energy, such as by a inductively coupled flywheels, impeller/turbine systems, or the use of speakers, jets or flow of a carrier medium to transfer (add or remove) heat.

"Transferring Heat" shall denote any transfer of heat or thermal energy to or from a physical entity. This definition shall include heat transfer cooling of a sample, such as by using a thermopile with a reverse bias or using a bifurcated thermopile having reversed "p" and "n" type junctions.

Regarding electrode orientations, the invention is sometimes defined using the term "adjacent" such as where a container is adjacent a base thermopile. In this context, the word adjacent shall mean close to, next to, or merely proximate, in terms of intended thermal transfer effect.

It is also important to note that although the term thermal is used here, no limitation is meant or intended in terms of black body radiation frequencies or operating temperatures, i.e., it is not intended that there is a temperature limit involved, merely because the term thermal radiation is commonly used by lay persons to describe warm or hot surfaces that do not emit visible light detectable by the naked eye. High temperatures (e.g., 3000° K.) shall be included when the word thermal is used.

DETAILED DESCRIPTION OF THE INVENTION

Referring now to FIGS. 1–4, an arrayable thermal assay system using active/control base thermopiles according to the instant invention is shown. In FIGS. 1 and 2, cross sectional schematic side views of two thermal sensing arrays are given showing five cells C1, C2, C3, C4, and C5.

Cells C1–C5 can each contain sample containers as shown in FIG. 3, where a combination cross sectional/surface view of a sample and sample holder used in the thermal sensing array of FIGS. 1 and 2 is shown. Sample container S1 corresponding to cell C1 is thus shown, having an optional seal cap 7 and nestled or placed into a sample holder 101 that can be fabricated from many known materials of known thermal conductivity, such as numerical control-machined copper or aluminum, which has a low heat capacity or greater thermal conductivity. Sample container S1 can comprise any vessel or chamber into which a sample can be placed, such as reaction tubes, microtiter plates, microfuge tubes, pipettes, or micropipettes, preferably with capacities of 0.5 milliliters or less, including the lambda, straight bore, or Levy types. For example, sample container S1 can comprise a disposable glass or plastic microfuge tube such as available from Robbins Scientific (Sunnyvale, Calif.), as long as such tubes are fairly uniform in their dimensionality from tube to tube and similarly uniform in their thermal characteristics, such as heat capacitance. Typical tube or sample container volumes used with this invention are 200 microliters or less in volume. To increase thermal conductivity and reduce error in the inherent thermal resistance $R_0$, sample holder 101 can have a profile that matches closely that of the sample container S1, and an optional vacuum line VAC can be connected to a suction manifold which is designed to pull sample container S1 into tight thermal contact or communication with the sample holder 101. This increases thermal conductivity across the thermal interface (shown, Thermal Interface) between sample container S1 and sample holder 101. The environment around sample holder S1 can be under a partial vacuum, to reduce thermal cross-talk by convection between samples. Alternatively, the ambient space between samples and their respective cells can be filled with a gas (at atmospheric or greater pressure) having low thermal conductivity like helium, or a gas having a low water content, like dry nitrogen, to reduce evaporation and condensation effects, and to reduce outside diffusion or contamination. Sample fill volumes inside sample container S1 can vary, but preferably, fill volumes beyond the vertical extent of sample holder 101 should be avoided to reduce error due to a higher thermal resistance $R_0$. For a sample holder 101 that extends halfway up a 200 microliter sample container, an appropriate fill volume is 100 microliters, or 1/10 mL. Also, if desired, sample holder 101 can be used in lieu of sample container S1, or the sample holder 101 can be integral with the sample cell C1.

Referring now to FIG. 4, a combination cross sectional/surface view of a pair of samples and sample holders inside respective cells, separated by a differential thermopile, such as used in the thermal sensing array of FIGS. 1 and 2, is shown. Close packed cells C1 and C2 are shown containing respective sample containers S1 and S2 retained by respective sample holders 101. Cells C1 and C2 can be fabricated using many known materials and techniques, including castings, glass, or custom-machined metals such as aluminum. A known thermal contact is established between sample holders 101 and respective cells C1 and C2 using soldering, welding or other joining arts or techniques to provide ample thermal conductivity and freedom from movement or vibration. Care should be taken to select materials throughout that do not pose a risk of reaction, e.g., oxidation or altering of pH, to samples being tested. The case P of cells C1 and C2 should be smooth and of known profile to permit intimate thermal interfacing with one or more thermopiles, such as a differential thermopile DT12 as shown. Differential thermopile DT12, so named because its thermal contact spans cells C1 and C2, is used primarily to sense subtle temperature differences between cells C1 and C2. Thermopiles used throughout are of known construction, having opposed thermal junctions A and B as shown. Thermopiles are generally made from a number of thermocouples connected in series, each thermocouple being made from two junctions of dissimilar metals to provide either the Seebeck or Peltier effects on demand. For discussion of such devices and the Seebeck or Peltier effects, see e.g., Charles Kittel, *Introduction to Solid State Physics*, John Wiley and Sons (1976), and *Sensors And Actuators: State of The Art of Sensor Research and Development*, Eds. S. Middelhoek and J. Van der Spiegel, Elsevier Sequoia, 1987. In the Seebeck effect, a temperature difference across the opposed thermal junctions causes development of an electromotive force that is approximately proportional to the difference in the temperatures of the two opposed thermal junctions. The temperature difference is a direct thermodynamic result and can be read from standard tables, or obtained by prior calibration. In the Peltier effect, an electromotive force or bias applied across the opposed thermal junctions of a thermocouple or thermopile causes heat pumping and a resultant temperature difference between the two junctions, driven by a electric carrier flow-induced heat transfer mechanism. This typically causes one thermal junction to become cold, while the other becomes hot. See, Stanley W. Angrist, *Direct Energy Conversion* $4^{th}$ Ed., Allyn and Bacon, Boston, © 1982. Typical thermoelectric materials that provide the Seebeck and Peltier effects are semiconductors such as $Bi_2Te_3$, $PbTe$, or $GeTe$. Alternatively, a thermoelectric circuit can be made by welding together wires of pure metal or alloys such as copper with constantan, chromel with alumel, or platinum with a platinum-rhodium alloy, and these structures can be placed electrically in series to enhance the thermoelectric effects, as known by those of ordinary skill in the art. Commercially available thermopiles include those manufactured by Melcor Incorporated, Trenton, N.J.

Differential thermopile DT12 is placed in thermal contact between sample cells C1 and C2 primarily for sensing and control via use of the Seebeck effect, to provide accurate and sensitive measurement of the temperature difference between the cells. If the temperature ramping or changes occurring as a result of the assay are slow enough, there is a strong correlation between the temperature difference sensed between cells C1 and C2, and the actual temperature difference between samples held in sample containers S1 and S2 held inside cells C1 and C2. For arrays where sample spacing is on the order of a centimeter, the cell response time constant is on the order of 1 second. Although the interior of differential thermopile DT12 is shown having dissimilar junctions nearest its opposed thermal junctions A and B, any thermoelectric structure can be used that achieves the same result, including the use of remotely located opposed thermal junctions where thermal conductivity is mediated by use of a thermal bus or other thermal communicator, e.g., a copper strip or liquid filled body.

Referring once again to FIG. 1, one arrayable approach to a thermophysical assay can be given. Between each cell is a unique differential thermopile Dtxy, where x is the number of the cell in thermal contact with one of its opposed thermal junctions, and y is the number of the cell in contact with its other thermal junction. As shown, differential thermopile DT23 is in thermal communication with, and positioned between, both cells C2 and C3. This numbering system, and the placement of the differential thermopiles can be extended to 2 or 3 dimensions, as will be discussed below.

The approach given here to implement the assay begins with performing a heat transfer to the two or more sample cells, and samples, as shown. For this purpose, a base thermopile BT as shown, with similar operating principles and constructions as discussed above, has one of its opposed thermal junctions in thermal contact with the bottoms of cells C1–C5. Although for simplicity, the bottom of the cells is dedicated for this purpose, any surface or subsurface of the cells can be used, with or without the use of an added thermal bus. Base thermopile BT can be used to contact all cells as shown, or individual base thermopiles can be used instead, as discussed below and shown in FIG. 2. By applying an electromotive force or voltage to the base thermopile BT, heat can be applied or removed from cells C1–C5, although the typical operating mode for an assay calls for application of heat and a resultant temperature increase from initial ambient temperatures.

The other opposed thermal junction of base thermopile BT can be in thermal contact with an optional isothermal plane or plate (shown, Isothermal Plate) which can be fabricated from copper, or any other thermally known smooth material. The isothermal plate helps provide a steady heat sink for the base thermopile BT to draw from in providing a uniform heat transfer to the cells when acting as a heat pump. Optionally, to help along a process whereby the temperature of cells C1–C5 is ramped, a conventional resistive or other type of strip heater SH can be affixed to any part of the isothermal plate as shown, and driven using electrical leads SHL as shown to follow a desired temperature profile. The isothermal plate can be temperature-monitored using an independent device, not shown, for use in temperature/temperature difference calculations.

By using base thermopile BT to provide a metered heat transfer, a constant-slope heat transfer can be provided, with uniformity to all cells. Using prior calibration, one can exactly compensate for, or reduce the effect of, any anisotropies in thermal transfer such as thermal gradients that are inherent to the apparatus. This compensation provides precision and accuracy which is very helpful when trying to perform the thermophysical assay in a multisample array spread in two dimensions. The use of an isothermal plate can reduce anisotropies even further, assuming there is no significant source of unwanted thermal radiation nearby that is transferring to, or coupling into the plate.

Though the procedure can vary, and can be performed in a virtually unlimited number of ways, a finite heat transfer, such as measured in calories or Joules, is performed. In order to make use of the heat input, the actual heat transferred is determined or inferred from prior calibrations. For example, the effect of driving a particular base thermopile BT with an electromotive force of 5 volts for one second will transfer a known amount of thermal energy from the isothermal plate to the cells. In the absence of an isothermal plate, the ambient environment shall act like a heat sink, but convection and other hard-to-predict factors could make this less desirable, and it is best to maintain the isothermal plate at a set or known changing temperature to allow donating heat to the base thermopile BT when it is acting as a heat pump, with a minimum change in the temperature of the associated thermal junction of the base thermopile. Determining the heat transferred can comprise integrating the heat transfer rate with respect to time, or any equivalent steps in an algorithm.

Meanwhile, inside the sample containers (e.g., sample containers S1–S5 corresponding to sample cells C1–C5), different molecules having different thermal characteristics, or undergoing phase or thermal changes, can cause the temperatures of various samples to differ from one another. These temperature differences are then detected by the differential thermopiles Dtxy. The use of selected samples with known contents, i.e. reference samples, can facilitate this process.

Once temperature differences are known from an initial heat transfer by base thermopile BT, an additional heat transfer adjustment is performed by use of local heaters H1, H2, H3, H4, and H5 as shown, which are individually in thermal contact with respective cells C1–C5, or with the respective samples S1–S5, if desired. If the local heaters are two wire devices, each can have dual feed leads HL as shown. The purpose of the additional heat transfer adjustment is to drive the temperature difference between cells and their respective samples to zero. This provides essential data and reduces cross talk and thermal leakage, and makes data collection and error reduction easier. Any number of known algorithms can be used, and the local heaters H1–H5 can be used in any combination desired to bring about this result, so long as the size and source(s) (namely, the local heater responsible) for the additional heat transfer adjustment is determined or known. If, for example, a first sample inside sample container S1 becomes, as a result of the initial heat transfer, 10 microKelvin lower in temperature than its nearest neighbor, a second sample inside sample container S2, one can apply heat using the local heater H1 to bring the first sample "in line" to drive that temperature difference toward zero. By tracking or determining (via prior calibration, for example) the additional heat transfer adjustment value in calories or Joules, the heat capacitance of the sample can be obtained; by dividing by the sample mass, the heat capacity can be obtained, using elementary thermodynamic relationships. Using both the information from the operating history of the base thermopile BT for the assay and the operating history of each local heater Hx, one can derive the heat capacitance of each sample, aided by any reference samples of known composition and thermal characteristics "seeded" into the array to reduce data error and increase statistical confidence levels. By using the base thermopile BT in a control mode where the Seebeck effect is utilized, additional temperature data can be obtained for greater precision or error-check correlation.

In each case, a thermal signature for each sample can be generated, using the heat capacitance or thermal profile thus generated.

This process can be repeated, with initial bulk heat transfers performed by base thermopile BT followed by additional heat transfer adjustments performed by local heaters Hx. In conjunction with a temperature ramp at the isothermal plate, such an assay can sweep across temperatures of interest, such as a sweep from 25° C. to 95° C. in increments of 0.01° C./second for a scan of 7500 seconds, or any intervals, including shorter intervals, where ranking or comparing of samples can be done quickly. By following each heat transfer by base thermopile BT with a additional heat transfer adjustment by the local heaters, temperature differences are kept near zero, to reduce error.

Local heaters Hx can be selected from a large group of heat producing devices, such as commonly used resistive devices; non-ohmic devices, such as diodes; devices utilizing electromagnetic induction as an energy transfer method, such as microwave emitters; devices operating primarily by light emission, such as lamps or lasers; sonic devices, such as vibrating membranes; speakers; devices using combustion-based heating; devices that mediate exposure to one or more heat sinks, using modulatable barrier; any chemical device utilizing a phase transformation of a substance for heating; any mechanical system to convert mechanical energy to heat energy; or any device using Bernoulli flow of a carrier medium to transfer heat, such as air or fluid jets, as can be constructed by those with ordinary skill in the art.

As mentioned above, base thermopile BT does not have to be a single device that services all cells C1–C5. As shown in FIG. 2, a cross sectional schematic view of a thermal sensing array similar to that in FIG. 1 is shown, using differential thermopiles DTxy as before, but now with individual base thermopiles Btx (BT1–BT5), where x is the number of the cell serviced by the base thermopile. The assay procedure described above can be used, with the modification that the initial heat transfer using base thermopile BT can now be accomplished using individual base thermopiles, with the possibility open that a given cell, such as cell C1, for example, can get a customized or unique heat transfer from individual base thermopile BT1 with respect to other cells C2–C5. This allows customized heat transfers for greater speed and accuracy. Further, use of individual base thermopiles Btx allows individual temperature sensing using the Seebeck effect when such thermopiles are operated in the Seebeck effect mode, yielding more data to be used in determining a thermal signature for each sample.

Using the thermal assay system as shown in FIG. 2, new possibilities open up for an approach to an arrayable thermophysical assay. Instead of using individual base thermopiles Btx for the initial heat transfer, the local heaters can be used exclusively for this purpose, as well as for the subsequent additional heat transfer adjustments as described. This leaves individual base thermopiles Btx in control mode, where the Seebeck effect can be used to with perhaps greater accuracy to determine temperature differences between the cells C1–C5 and the isothermal plate. The local heaters can be relocated to take the place of, or exist adjacent to, the individual base thermopiles Btx as shown. The isothermal plate can then act as a heat sink if needed.

Generally, the temperature sensing data from the differential thermopiles Dtxy can be used in a weighted fashion to help drive cell temperature differences to zero. The differential thermopile Dtxy can also be arranged in a two dimensional array.

Referring now to FIG. 5, a possible cross sectional top view of cells and differential thermopiles of a 3×3 cell thermal sensing array using either base thermopiles or individual base thermopiles is shown. With such a two dimensional array, cells are now labeled Cxy using matrix notation, with two digits, a row and column number, e.g., cell C31 being in the third row, first column, as shown. Inside cells Cxy are sample containers Sxy as shown, such as sample container S12 inside cell C12 as indicated. Cells Cxy have cases Pxy in analogy with this notation, as shown with case P13. With such a 3×3 array, a given cell can be surrounded by, and in thermal contact with, up to four differential thermopiles DTabcd, where a and b are the row and column number of a first cell with which it is in thermal contact, and c and d are the row and column number of a second cell with which it is in thermal contact, as shown, with twelve such differential thermopiles DTabcd shown. Well known weighted summation loop techniques can be used in the procedure above to help bring neighboring cell temperatures into alignment. For example, the cell denoted as C22 shown in the center of the 3×3 array can have corrective additional heat transfer adjustments made primarily on the basis of temperature differences of only its neighboring cells, via differential thermopile DT2122, DT1222, DT2223, and DT2232, with preferential weighting given to those differential thermopiles.

Figure 6:
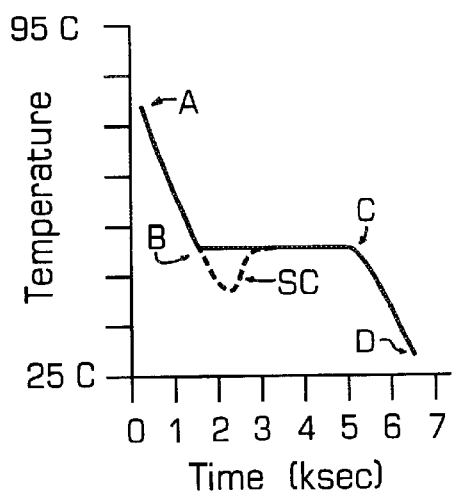
FIG. 6 shows a temperature versus time thermal curve for a single system.
Figure 7:
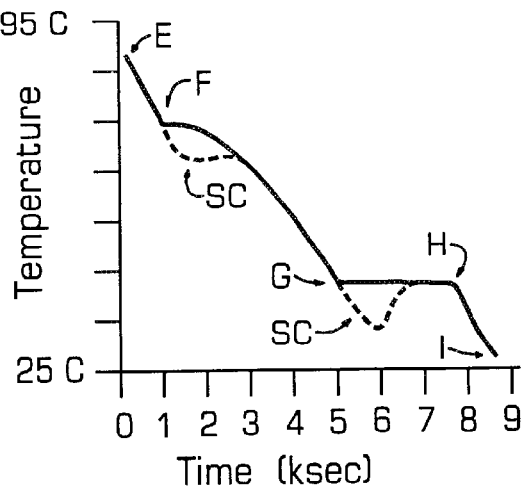
FIG. 7 shows a temperature versus time thermal curve for a binary system.

This arrayable thermal assay system can be used to derive thermal signatures for samples where binding or other events have already taken place, or it can derive heat transferred versus temperature data that can be used to elucidate reactions or phase transformations as they happen. With data easily collected that represents the total heat transferred to any sample, one can identify phase transitions as a function of total heat input, during a scan of temperature. To illustrate, a conventional temperature versus time cooling curve is shown in FIG. 6, for a single system, that is for a single type of phase transformation (e.g., crystallization) process. Here, temperature is ramped downward, such as would happen if the isothermal plate described above were ramped downward as a linear function of time, e.g., downward by 0.01° C./second. Between points A and B as shown, the temperature descends linearly with time. Between points B and C, a phase transformation is occurring, and temperature remains constant until the phase transformation (e.g., freezing) is complete. The dotted portion labeled SC starting at point B shows the effect of any supercooling. After point C, the phase transformation is complete and the temperature again descends, ending at point D. In FIG. 7, a similar cooling curve is shown for a binary system displaying two phase transformations, e.g., condensation and freezing. The temperature at point E descends linearly until point F, at which point a flat shoulder is encountered during a first phase transformation, with possible supercooling shown using the dotted line labeled SC starting at point F. After another descent in temperature, a second phase transformation is shown between points G and H, with possibly supercooling again shown using dotted line SC starting at point G. After the second phase transformation at G-H, temperature again descends until point I is reached. Generally, due to a mixture of molecular structures, phase transformations on a cooling curve can be indicated as a shoulder or change in slope as seen starting at point F.

Figure 8:
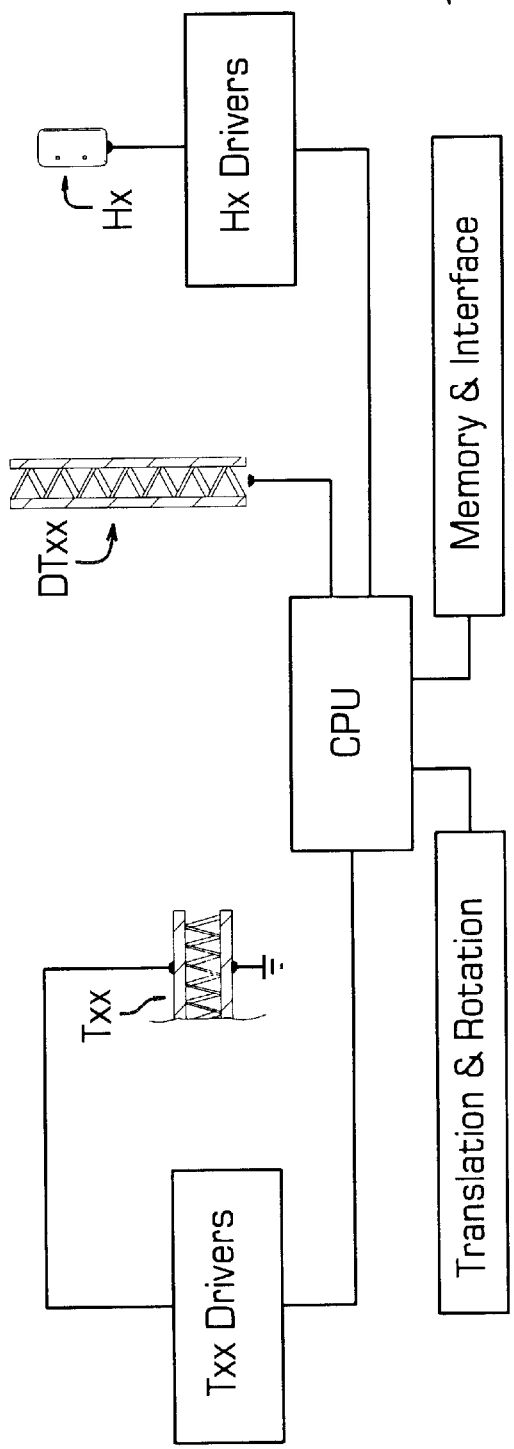
FIG. 8 shows a general schematic diagram for a control and interface system to perform a thermal assay according to the present invention.

FIG. 8 shows a general schematic diagram for a control and interface system to perform a thermal assay according to the present invention. On the left as shown, driver circuitry Txx Drivers interface with base thermopiles or individual base thermopiles Txx as shown. The design and construction of such driver circuitry is well known in the electronic arts, and can perform two functions consistent with the twin modes of the thermopiles, using the Seebeck and Peltier effects. Such drivers would, for example, apply appropriate voltages while the thermopile in question is in Peltier (heat pump) mode, and would monitor its Peltier voltage application history to calculate or retain an integrated heat transfer value, if needed, in conjunction with a central processing unit or CPU to which they are connected, as shown. Such drivers would also collect developed voltages arising from temperature differences between sample cells found by thermopiles using the Seebeck effect, and would integrate or otherwise record such voltages for use by the CPU. In a similar way, the CPU can also collect, with or without an intermediary driver or set of drivers (not shown), the developed voltages from all differential thermopiles Dtxx as shown. Similarly, driver circuitry can be devised to provide driving voltages for, and monitor operation history of, all local heaters Hx, as shown, with interfacing with the CPU as shown. The CPU can store and execute known algorithms based on those used in DSC (Differential Scanning Calorimetry) to provide thermal signatures, such as rankings or absolute determinations of heat capacitances. Heat capacities Cp can be determined by dividing the heat capacitance for a sample by the sample mass, which can be determined using other methods, or other devices which can be made part of this assay system. Rankings of samples by their respective thermal signatures and other data can be made available by the CPU to memory and user interface devices (Memory & Interface) as shown, and known in the electronic arts. Similarly, if robotic movements or sample motions are desired, the CPU can provide thermal signature or ranking information for use by a driver for sample translation through three-dimensional space and rotation about two axes, shown as Translation & Rotation.

Through instruction set programming as known in the art, the CPU can use the sensing or control data provided by the various differential thermopiles and base thermopiles and use the monitoring data which tracks the active mode (heat pumping) history of base thermopiles and local heaters to provide the heat transferred and additional heat transfer adjustments needed for all calculations as is done on a smaller scale for DSC (see above equations (1)–(4)). Use of base thermopiles make the assay arrayable, in providing fine control and active mode modulation of the heat transfers, and eliminating thermal gradients which are otherwise problematic using conventional techniques.

For this thermal assay to work, highly sensitive temperature sensing is needed when detecting heat capacity or temperature changes in small amounts of materials. This requires low noise amplifiers to amplify, without much distortion, the small voltages generated by the differential thermopiles and base thermopile when they are in control or Seebeck mode. A problem from a standpoint of drift presents itself: calorimetry is best done using slowly varying quantities, including active signals used for heat transfers (e.g., Peltier effect pumping), of frequency less than 1 Hz. In this frequency region, control (sensed) frequencies from the thermopiles detecting temperature differences in Seebeck mode will be at or around 1 Hz frequencies as well. At such low frequencies, most amplifiers exhibit 1/f noise and drifts with temperature which interfere with signal recognition.

Figure 9:
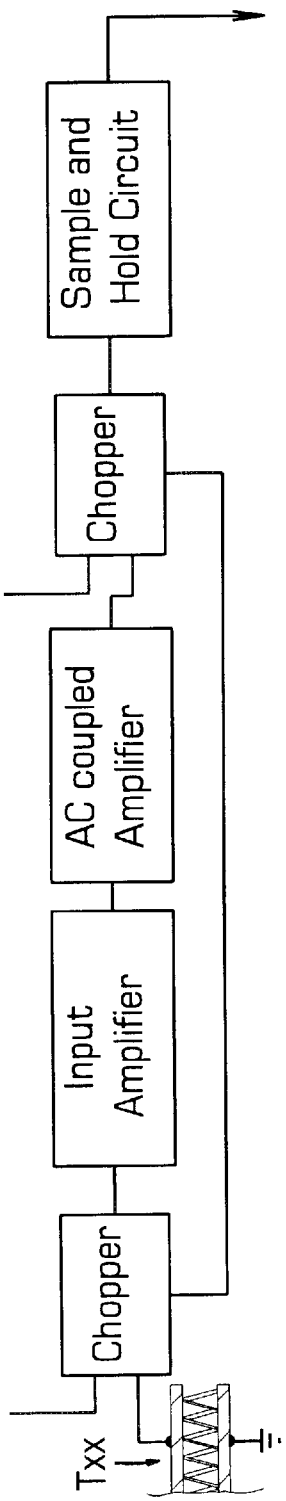
FIG. 9 shows a general schematic diagram for a correlated double sampling system to reduce noise and drift from calorimetric determinations.

FIG. 9 shows a general electrical schematic diagram for a correlated double sampling system to reduce noise and drift from calorimetric determinations using this invention, while amplifying a thermopile output voltage signal. A thermopile Txx is shown, which can be a differential thermopile or a base thermopile, where small Seebeck voltages are generated, indicative of minute temperature differences encountered between its opposed thermal junctions. The Seebeck output voltage from thermopile Txx is supplied to an Input Amplifier as shown, but not directly. Instead, using the Chopper as shown, the input amplifier is switched back and forth between a Reference voltage as shown and the thermopile Seebeck output. This chopped AC signal is then amplified with an AC Coupled Amplifier as shown, which blocks the slowly changing amplifier drifts, as known in the art. At the output of the AC Coupled Amplifier, another Chopper (or chopper section) synchronous with the input chopper switches between a Reference as shown and the amplifier output. A known Sample and Hold Circuit then samples the chopped amplifier output and reconstructs and outputs the Input Waveform as shown for use by a driver or CPU. Because the input and output from the two amplifiers spend so much time at the reference voltage, drift is minimized. With the AC coupled amplifiers, 1/f noise is reduced, and can be reduced further by increasing the chopper frequency. This AC based processing technique enhances the overall signal/noise ratio of the Seebeck potentials, and can be used to increase sensitivity to further reduce requisite sample volumes, which allows closer packing on an array, and faster, more accurate calorimetric measurements.

Figure 10:
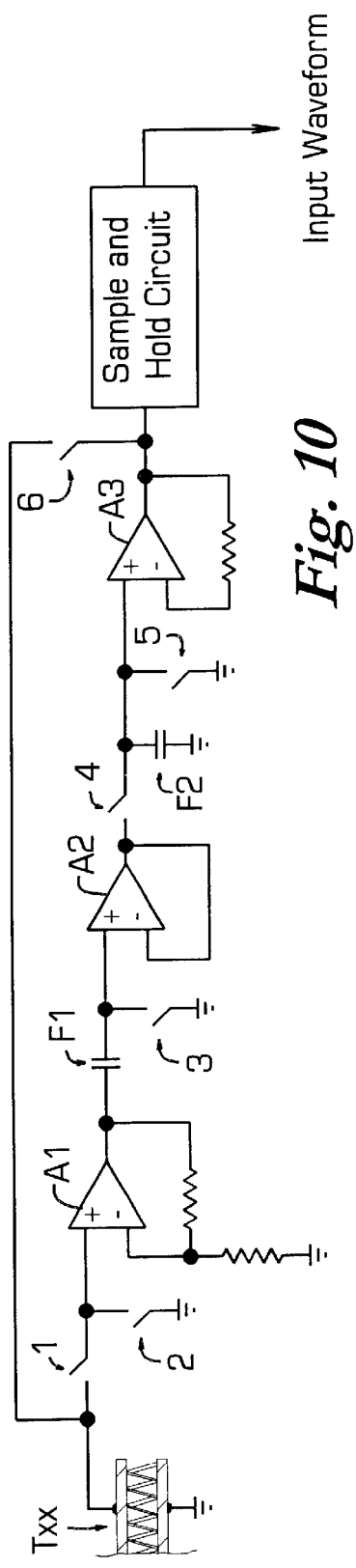
FIG. 10 shows a sample circuit diagram to effect the correlated double sampling suggested by FIG. 9.

FIG. 10 shows a sample circuit diagram to effect the correlated double sampling indicated in FIG. 9. On the left as before, a thermopile Txx provides a Seebeck output, supplied to the non-inverting input of an operational amplifier A1 through switch 1 as shown. This feed to the non-inverting input can also be selected grounded via switch 2 as shown. Operational amplifier A1 has an external feedback resistor circuit as shown on its inverting input terminal, to provide gain at the operational amplifier output, which is connected to one side of reference storage capacitor F1. The other side of reference storage capacitor F1 is fed to the non-inverting input of operational amplifier A2, and can be grounded via switch 3 as shown. Operational amplifier A2 has a straight external feedback loop on its inverting end to provide unitary gain, acting as a buffer. At the output end of operational amplifier A2 a switch 4 allows output to a sample storage capacitor F2, while switch 5 allows selective grounding, as shown. This same output is then fed to a third amplifying non-inverting operational amplifier A3 whose output can be fed to a Sample and Hold Circuit as shown, which will in turn prepare an Input Waveform as shown, for use by drivers and/or a CPU. Optional switch 6 allows the output of operational amplifier A3 to be selectively fed back to thermopile Txx as shown. As will seen by those skilled in the art, closing switches 2 and 3 will store a reference voltage on the reference storage capacitor F1, while closing switches 1 and 4 will store the sample or signal from thermopile Txx on sample storage capacitor F2. These paired switching actions can be done by the Chopper shown in FIG. 8, to accomplish the switching described between a reference voltage and an amplifier output. Optionally, an additional feature allows driving the thermopile Txx in active mode upon closing switches 5 and 6, which feeds a reference voltage back to the thermopile Txx, via a possible driver circuit, not shown.

Figure 11:
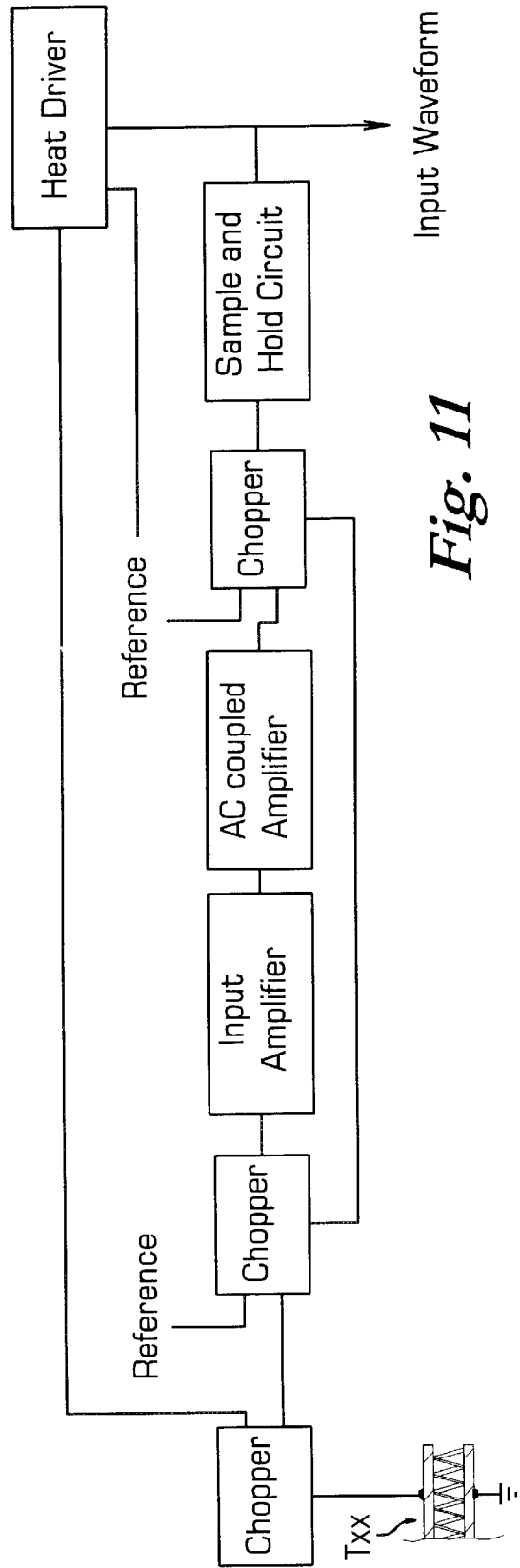
FIG. 11 shows a general schematic diagram for a correlated double sampling system similar to that shown in FIG. 9, with an added circuit to allow driving one or more thermopiles in active mode(s).

FIG. 11 shows a general schematic diagram for a correlated double sampling system similar to that shown in FIG. 9, with added circuit to allow driving one or more thermopiles Txx in active mode. This schematic is functionally similar to that shown in FIG. 9, but with the Chopper function added on the left to allow synchronized feeding of the output of a heat driver circuit (Heat Driver) as shown to the thermopile Txx during the "reference" cycle of the chopper. The heat driver circuit is connected to the output of the Sample and Hold Circuit so that it can make use of the Seebeck detected voltage information, and it allows cyclic driving of the thermopile Txx—whether it is a base thermopile, or an individual base thermopile—while it is sensing a temperature difference. This allows fine adjustments to be made on the samples during an assay, consistent with programmed instructions in a CPU. This allows not only temperature ramping, but customized thermal input in response to any possible reaction in a sample, "massaging" a reversible phase transformation, for example, by reversing a temperature ramp, repeatedly if necessary, to elucidate a thermal mechanism or signature for the sample.

In addition to the DC voltages applied above to control the rate of active mode heating by the base thermopiles, a small, slowly varying (1 Hz or less, typically) AC voltage can be applied to the base thermopiles to create a time varying rate of heat transfer. With this method, the thermal conductivity and the thermal capacitance of the samples can be measured directly, a known technique borrowed from other thermal assay methods.

The thermal impedance of a system can be generally be viewed as consisting of a heat conductance, G, and a capacitance, C. An AC waveform to improve signal to noise for analyzing thermal impedance can be used in the following manner: if the excitation (input) waveform is a sinusoidal input like Acos(wt) and the sample thermal system is linear, the response (output) from the sample system will be Bcos(wt+f), where A is the excitation amplitude, B is the response amplitude of a given sample, w is the frequency of excitation, t is the time at which the measurement is made, and f is the phase shift induced by thermal capacitance. To analyze the system response, the input and output are multiplied (either by a microprocessor CPU or by an analog multiplier) to get ABcos(wt)cos(wt+f). An equivalent form of this product is ABcos(f)+ABcos(2 wt+f); by filtering out the 2 wt term, the phase information, ABcos(f), is preserved and can be used to get the thermal conductance of a sample. Similarly, multiplying the output by a quadrature term, Asin(wt), the product ABsin(wt)cos(wt+f) can be rewritten as ABsin(f)+ABsin(2 wt+f); again, by filtering out the 2 wt term, the phase information ABsin(f) is preserved and can be used to get the heat capacitance of a sample. The heat capacitance C is directly proportional to ABsin(f) and can be determined directly by calibrating the system with a reference, such as deionized water. For example, if the heat capacitance of water measured by the system is $CW_w = AB_w\sin(f_w)$, then the heat capacitance of a sample, $C_s = AB_s\sin(f_s)$, can be obtained as $C_s/C_w = B_s\sin(f_s)/B_s\sin(f_s)$. Since the heat capacitance of water is tabulated, the heat capacitance can be calculated directly. See signal processing references such as *Computer Image Processing and Recognition*, E. L. Hall, Academic Press, 1979.

In addition to the methods described above, temperature or temperature differences can be monitored by thermopiles, infrared detectors such as semiconductor infrared detectors, pyroelectric devices (which are sensitive to time rate of change), semiconductor diodes, metal-metal thermocouples, bimetallic levers, metal-semiconductor levers, and other devices known in the art.

Using this teaching, arrayable thermal assays are made possible without previous problems with thermal gradients and poor sample temperature sensing and control. Obviously, many modifications and variations of the present invention are possible in light of the above teaching. It is therefore to be understood, that within the scope of the appended claims, the invention can be practiced otherwise than as specifically described or suggested here.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

What is claimed:

1. A method for performing thermal assays on a first sample and a second sample in an array, the method comprising:
   (a) performing a heat transfer to the first and second samples, using one or more base thermopiles in thermal communication with separate containers for the samples; and
   (b) determining a total heat transferred to the samples by one or more base thermopiles in step (a); and
   (c) sensing in real time, with a thermopile located between, and in contact with, the containers for the first and second samples, a temperature difference between a first sample and a second sample of the two or more samples resulting from performing step (a).

2. The method of claim 1, comprising:
   (d) performing an additional heat transfer adjustment on the basis of the temperature difference, the additional heat transfer adjustment sized and targeted to at least one of the first and second samples to drive the temperature difference toward zero between the first and second samples; and
   (e) determining the size of the additional heat transfer adjustment during step (d) for each of the first and second samples.

3. The method of claim 2, wherein the heat transfer adjustment comprises applying heat directly using a local heater.

4. The method of claim 2, additionally comprising:
   (f) comparing the size of the additional heat transfer adjustment during step (e) for each of the first and second samples, and generating therefrom a thermal signature from successive applications of the method during a ramp in temperature of at least one of the first and second samples.

5. The method of claim 1, wherein the heat transfer using the base thermopile occurs with respect to an isothermal plate in thermal communication with a junction of the base thermopile.

6. The method of claim 5, wherein the isothermal plate is in thermal communication with a strip heater, and the method additionally comprises: ramping the temperature of the isothermal plate using the strip heater.

7. The method of claim 1, wherein step (a) comprises applying an AC waveform to drive the base thermopile, thereby creating a time varying rate of heat transfer by the base thermopile.

8. A method for performing thermal assays on a first sample and second sample in an array, the method comprising:
   (a) performing a heat transfer to the first and second samples, using a local heater in thermal communication with containers for the samples;
   (b) determining a total heat transferred to the samples by the local heater in step (a); and
   (c) sensing in real time, with a thermopile located between, and in contact with, the containers for the first and second samples, a temperature difference between a first sample and a second sample resulting from performing step (a).

9. The method of claim 8, comprising:
   (d) performing an additional heat transfer adjustment on the basis of the temperature difference, the additional heat transfer adjustment sized and targeted to at least one of the first and second samples to drive the temperature difference toward zero between the first and second samples; and
   (e) determining the size of the additional heat transfer adjustment during step (d) for each of the first and second samples.

10. The method of claim 9, additionally comprising:
    (a) comparing the size of the additional heat transfer adjustment during step (e) for each of the first and second samples, and generating therefrom a thermal signature from successive applications of the method during a ramp in temperature of at least one of the first and second samples.

11. The method of claim 8, wherein step (a) comprises applying an AC waveform to drive the local heater, thereby creating a time varying rate of heat transfer by the local heater.

12. The method of claim 8, wherein the heat transfer using the local heater occurs with respect to an isothermal plate in thermal communication with the local heater.

13. An arrayable thermal assay apparatus using base thermopiles comprising:
   (1) one or more base thermopiles in thermal contact with a first sample container and a second sample container, each of the containers adapted to retain a sample;
   (2) a differential thermopile located between the first and second sample containers with a (a) first opposed thermal junction in thermal contact with the first sample container and (b) a second opposed thermal junction in thermal contact with the second sample container; and
   (3) first and second local heaters in individual thermal contact with the first and second containers, respectively, wherein the one or more base thermopiles are configured and driven to perform heat transfer to the first and second sample containers, the differential thermopile is configured and monitored to sense a relative temperature difference between the first and second sample containers, and wherein the first and second local heaters are configured and driven to perform an additional heat transfer adjustment on the basis of the relative temperature difference.

14. The arrayable thermal assay apparatus of claim 13, wherein the first and second sample containers comprises wells in a microtiter plate comprising additional wells, and wherein the apparatus comprises components of (1) through (3) for additional pairs of the wells.

15. The arrayable thermal assay apparatus of claim 14, wherein base thermopiles comprise an individual base thermopile in thermal communication with fewer than all of the wells having corresponding components (1) through (3).

16. The arrayable thermal assay apparatus of claim 13, further comprising a correlated double sampling system to reduce noise and drift from calorimetric determinations, the correlated double sampling system comprising:

an input amplifier connected to provide gain for a thermopile output signal from at least one thermopile selected from the group consisting of a base thermopile and a differential thermopile;

an AC coupled amplifier connected to provide gain to an input amplifier output signal from the input amplifier;

a sample and hold circuit having a sample and hold input connected to an output signal of the AC coupled amplifier; and a chopper circuit to cycle an input amplifier input signal to the input amplifier between the thermopile output signal and a reference voltage, and to also cycle synchronously the sample and hold input between an AC coupled amplifier output signal from the AC coupled amplifier and the reference voltage.

* * * * *